United States Patent [19]

Miesel

[11] 4,000,295
[45] Dec. 28, 1976

[54] 4-SUBSTITUTED-5,7-DINITRO-2-($\alpha,\alpha$-DIFLUOROALKYL)-BENZIMIDAZOLE COMPOUNDS AS INSECTICIDES

[75] Inventor: John L. Miesel, Indianapolis, Ind.

[73] Assignee: Eli Lilly and Company, Indianapolis, Ind.

[22] Filed: June 20, 1975

[21] Appl. No.: 588,972

Related U.S. Application Data

[60] Continuation of Ser. No. 415,100, Sept. 10, 1973, abandoned, which is a division of Ser. No. 221,809, Jan. 28, 1972, Pat. No. 3,790,595, which is a continuation-in-part of Ser. No. 833,685, June 16, 1969, abandoned.

[52] U.S. Cl. .............................. 424/273; 424/244; 424/267

[51] Int. Cl.$^2$ .......................................... A01N 9/22
[58] Field of Search ........... 424/244, 258, 267, 273

[56] References Cited

UNITED STATES PATENTS

| | | | |
|---|---|---|---|
| 3,418,318 | 12/1968 | Lambie et al. | 424/273 |
| 3,448,115 | 6/1969 | Holan et al. | 260/309.2 |

*Primary Examiner*—V. D. Turner
*Attorney, Agent, or Firm*—Joseph A. Jones; Everet F. Smith

[57] ABSTRACT

4-Substituted-5,7-dinitro-2-($\alpha,\alpha$-difluoroalkyl)-benzimidazole compounds and their alkali metal and alkaline earth metal salts, useful as insecticides.

11 Claims, No Drawings

4-SUBSTITUTED-5,7-DINITRO-2-($\alpha,\alpha$-DIFLUOROALKYL)-BENZIMIDAZOLE COMPOUNDS AS INSECTICIDES

CROSS-REFERENCE TO RELATED APPLICATION

This is a continuation of my copending application Ser. No. 415,100, filed Sept. 10, 1973, now abandoned, which is a division of my then copending application, Ser. No. 221,809, filed Jan. 28, 1972, now U.S. Pat. No. 3,790,595, which was a continuation-in-part of my then copending application, Ser. No. 833,685, filed June 16, 1969, now abandoned.

SUMMARY OF THE INVENTION

The present invention is directed to compounds of the formulae

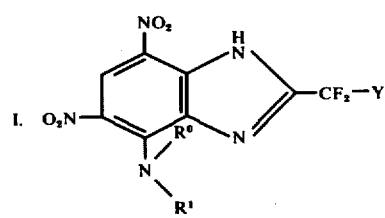
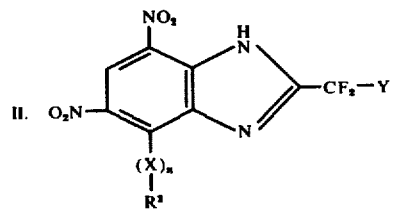

wherein Y represents
 a. hydrogen,
 b. chlorine,
 c. fluorine,
 d. trifluoromethyl, or
 e. pentafluoroethyl;
wherein
 a. when each of $R^0$ and $R^1$ is taken separately, each independently represents, subject to the limitation that at least one of $R^0$ and $R^1$ contains more than 1 carbon atom and that $R^0$ and $R^1$ together contain less than 14 carbon atoms:
  1. hydrogen,
  2. alkyl,
  3. alkenyl containing more than 2 carbon atoms,
  4. alkenyl containing more than 2 carbon atoms,
  5. (fluoroalkyl)methyl wherein alkyl is $C_1-C_7$, both inclusive, and bears at least one fluorine atom,
  6. cycloalkyl of $C_3-C_8$, both inclusive,
  7. cycloalkylloweralkyl, wherein cycloalkyl is from $C_3-C_8$, both inclusive, and loweralkyl is from $C_1-C_4$, both inclusive,
  8. loweralkylcycloalkyl, wherein cycloalkyl and loweralkyl are as defined in the preceding candidate moiety,
  9. adamantyl,
  10. benzyl,
  11. substituted benzyl wherein each substituent is loweralkyl of $C_1-C_4$, loweralkoxy of $C_1-C_4$, halo, nitro, trifluoromethyl, or cyano, there being from 1 to 5, both inclusive, substituents when each substituent is loweralkyl, loweralkoxy, or halo, and there being not more than 2 substituents when one substituent is nitro, trifluoromethyl, or cyano,
  12. decahydronaphthyl, or
  13. norbornyl; or
 b. when $R^0$ and $R^1$ are taken together, they jointly constitute, with the nitrogen atom to which they are attached, a heterocyclic radical which is:
  1. piperidino,
  2. hexahydroazepino,
  3. octahydroazocino,
  4. piperidino substituted by from 1 to 3 $C_1-C_4$, both inclusive, loweralkyl substituents, the total number of carbon atoms in all substituents being not in excess of 6,
  5. 1,2,3,4-tetrahydroquinolyl,
  6. decahydroquinolyl,
  7. 1,2,3,4-tetrahydroisoquinolyl,
  8. decahydroisoquinolyl, or
  9. azabicycloalkanyl of the formula

wherein Q represents $+CH_2+_2$ or $+CH_2+_3$, Q' represents $-CH_2-$ or $+CH_2+_2$, and Q'' represents

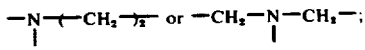

and wherein X represents oxygen or sulfur; $n$ represents 0 or 1; and $R^2$ represents
 1. alkyl of $C_1-C_8$, both inclusive, carbon atoms;
 2. alkenyl of $C_3-C_8$, both inclusive, carbon atoms;
 3. cycloalkyl of $C_5-C_7$, both inclusive;
 4. cycloalkylmethyl, wherein cycloalkyl is as defined in the preceding candidate moiety;
 5. loweralkylcycloalkyl, wherein loweralkyl is of $C_1-C_4$, both inclusive, and cycloalkyl is as defined in the preceding candidate moiety;
 6. 2-norbornyl; or
 7. decahydronaphthyl.

The above-described compounds exhibit insecticidal activity; hence, the present invention is also directed to insecticidal methods employing, and compositions comprising, the above-described compounds.

DETAILED DESCRIPTION OF THE INVENTION

Formulae employed throughout the present specification are predicated on the assumption that the proton on the imidazole portion of the benzimidazole ring is affixed at a ring position arbitrarily designated as "1":

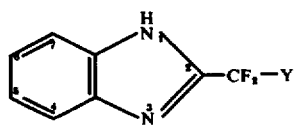

However, this proton may not be fixably attached to a specific ring nitrogen atom. Rather, it is believed that the compounds typically exist as tautomers, e.g.:

ever, it is generally preferred to hold the reaction mixture for a period of time to insure maximum yields. Temperatures higher than room temperatures are often

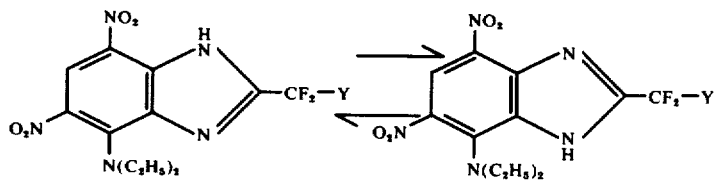

Therefore, the formulae herein, while showing the proton fixably positioned for the sake of uniform representation, are employed to designate either of the tautomeric forms or the more typical tautomeric mixture.

The compounds of the present invention are typically crystalline solids, of yellow to orange color. Except for the compounds of Formula II where $n = 0$, they are prepared by reacting a 4-chloro-5,7-dinitro-2-($\alpha,\alpha$-difluoroalkyl)benzimidazole of the formula

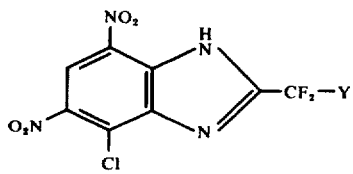

The identity of the other reactant varies with that of the final product desired. In the case of compounds of Formula I, the second reactant is an amine of the formula

and the reaction is carried out in the presence of a hydrogen halide acceptor, which can be any tertiary amine or an additional portion of the amine reactant. In the case of the compounds of Formula II for which the reaction is suitable, the second reactant is an alkali metal derivative of an alcohol or mercaptan of the formula $R^2$-XH. Regardless of the identity of the particular reactants, the reaction is conveniently conducted in an inert liquid reaction medium, and goes forward over a wide range of temperatures, such as from room temperature to reflux temperatures.

In carrying out the reaction, the reactants, or reactants and hydrogen halide acceptor, are contacted with one another in the reaction medium. The reaction goes forward readily yielding some of the desired 4-substituted-5,7-dinitro-2-($\alpha,\alpha$-difluoroalkyl)-benzimidazole product and tertiary organic amine hydrogen halide product or alkali metal halide at once; however, it is generally preferred to hold the reaction mixture for a period of time to insure maximum yields. Temperatures higher than room temperatures are often preferred. In the case of compounds of Formula I, reflux temperatures are generally preferred. The product so obtained can be separated from the reaction mixture by conventional methods. Typically, the by-product salt precipitates in the reaction mixture and is removed by filtration and solvent thereafter removed by evaporation to separate the desired product as a residue. Such product residue can be purified, if desired, in conventional procedures, typically recrystallization.

In the instance of the compounds of Formula II wherein $n = 0$, other synthetic routes are necessary. In one such synthetic route, a 3-$R^2$-o-phenylenediamine, for example, 3-methyl-o-phenylenediamine, is reacted with trifluoroacetic in conventional procedures. The resulting benzimidazole:

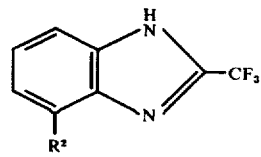

is then nitrated in conventional procedures to yield the desired compound of the present invention. In the case of products where the 2-substituent is pentafluoroethyl or heptafluoropropyl, the nitration is preferably conducted step-wise, the first nitro group being introduced with a mild nitrating agent, for example, potassium nitrate in sulfuric acid at 40° C., the second, with fuming nitric acid and fuming sulfuric acid.

Other synthetic routes are necessary where the 3-$R^2$-o-phenylenediamine is not readily available. In a first alternate reaction route, an alkyl nitrobenzimidazole is reduced to an alkyl aminobenzimidazole which is diazotized and the resulting diazonium group replaced by hydrogen:

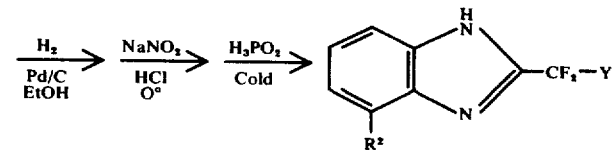

The resulting benzimidazole is then nitrated. As discussed above, step-wise nitration is preferred in the instance of the higher perfluoroalkyl groups. Otherwise, individual reactions are conducted in accordance with conventional procedures, as exemplified hereinbelow.

In the instance of alkyl groups bearing no alpha-branching, a yet other synthetic route is useful. This route is schematically described as follows, wherein $R^3$ represents hydrogen or alkyl:

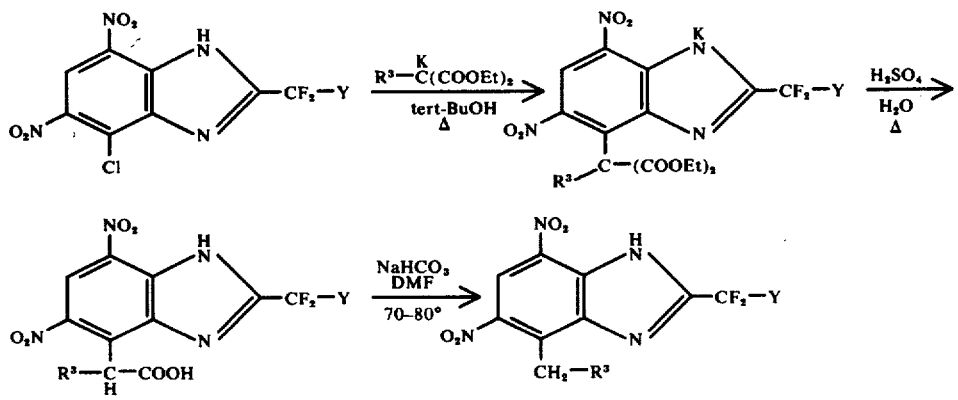

Each individual reaction is conducted in accordance with conventional procedures, as exemplified below.

Those compounds of the present invention which are alkali metal and alkaline earth metal salts are prepared by reacting the compounds of the present invention whose preparation is described above

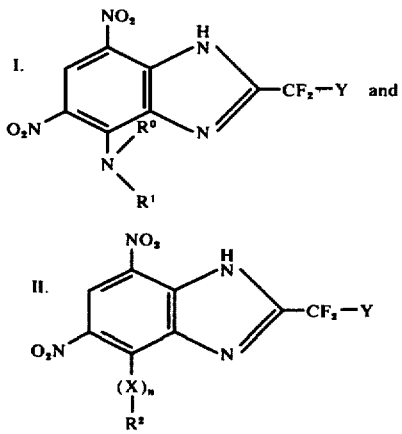

with an alkali metal alkoxide or an alkaline earth oxide. This reaction goes forward under temperatures of a wide range, such as from 20° to 120° C. An inert liquid reaction medium is necessary for good results; the loweralkanols are especially suitable for this purpose.

In carrying out the reaction, the reactants and solvent are contacted with one another in any way, and the resulting reaction mixture maintained in the reaction temperature range for a period of time. Solvents and by-product loweralkanol are then removed, conveniently by evaporation under subatmospheric pressure, to obtain the desired product as a residue. Purification can be carried out in conventional procedures if desired, typically by recrystallization.

The following examples illustrate the synthesis of the compounds of the present invention and will enable those skilled in the art to practice the present invention.

EXAMPLE 1

4-tert-BUTYLAMINO-5,7-DINITRO-2-TRI-FLUOROMETHYLBENZIMIDAZOLE

4-Chloro-5,7-dinitro-2-trifluoromethylbenzimidazole (5.0 grams) was mixed with 1.6 grams of triethylamine and 1.2 grams of tert-butylamine in a small amount of ethanol. The resulting reaction mixture was refluxed over a weekend, then poured into water and the resulting aqueous mixture acidified and filtered to separate the expected 4-tert-butylamino-5,7-dinitro-2-trifluoromethylbenzimidazole product. It was recrystallized from ethanol as an orange solid, m.p., 195°–97° C. Elemental analysis confirmed the identity of the product. A second crop melted at 177°–88° C.

Analysis, Calc. for $C_{12}H_{12}F_3N_5O_4$: C, 41.50; H, 3.48; N, 20.17. Found: C, 41.48; H, 3.51; N, 19.91.

EXAMPLE 2

4-tert-BUTYLAMINO-5,7-DINITRO-2-TRI-FLUOROMETHYLBENZIMIDAZOLE SODIUM SALT 4-tert-Butylamino-5,7-dinitro-2-trifluoromethylbenzimidazole (7.0 grams of compound prepared as described in Example 1) was mixed and reacted with 1.1 grams of sodium methoxide in about 200 milliliters of methanol. Most of the methanol was then removed on a rotary evaporator, and remaining traces of methanol were removed in a vacuum oven. As a result of these operations, there was obtained directly the expected 4-tert-butylamino-5,7-dinitro-2-trifluoromethylbenzimidazole sodium salt. IR analysis confirmed the identity of the compound by virtue of the absence of the N-H bond of the starting material. The identity was also confirmed by NMR and by elemental analysis.

EXAMPLE 3

4-PIPERIDINO-5,7-DINITRO-2-TRIFLUOROME-THYLBENZIMIDAZOLE

Triethylamine (1.0 gram; 0.00968 mole) was added to 3.0 grams of 4-chloro-5,7-dinitro-2-trifluoromethylbenzimidazole (0.00968 mole) in 200 milliliters of benzene. There was then added dropwise 0.8 gram of piperidine (0.00968 mole) in 10 milliliters of benzene. The resulting reaction mixture was refluxed overnight, cooled, an amount of ether added, and the mixture filtered. The filtrate was evaporated, yielding the desired 4-piperidino-5,7-dinitro-2-trifluoromethylbenzimidazole product as an orange solid. It was recrystallized from benzene as a light brown solid, m.p., 199°–206° C. NMR analysis confirmed the identity but suggested the presence of a small amount of triethylamine.

Analysis, Calc. for $C_{13}H_{12}F_3N_5O_4$: C, 43.45; H, 3.36; N, 19.49. Found: C, 43.73; H, 3.52; N, 19.38.

EXAMPLE 4

4-tert-BUTYLAMINO-5,7-DINITRO-2-DIFLUOROMETHYLBENZIMIDAZOLE

4-Chloro-5,7-dinitro-2-difluoromethylbenzimidazole (1.9 grams), triethylamine (0.7 gram), and tert-butylamine (0.5 gram) were mixed in ethanol and refluxed overnight. The mixture was then poured into water, acidified, and filtered to separate the expected 4-tert-butylamino-5,7-dinitro-2-difluoromethylbenzimidazole product, m.p., 189°–196° C. After recrystallization from ethanol, it melted at 199°–201° C. The identity of the product was confirmed by NMR analysis.

EXAMPLE 5

4-CYCLOHEXYLOXY-5,7-DINITRO-2-TRIFLUOROMETHYL BENZIMIDAZOLE

Cyclohexanol (5.4 grams) and potassium (1.9 grams) were reacted in 50 milliliters of dry hexamethylphosphoric triamide. When reaction had ceased, the solution was stirred and 5 grams of 4-chloro-5,7-dinitro-2-trifluoromethylbenzimidazole were added. Stirring was continued overnight. The reaction mixture was then poured into water, acidified, and extracted with ethyl acetate. The ethyl acetate was then removed by evaporation, and the residue was chromatographed on 300 milliliters of silica gel using benzene as eluant. The benzene was removed by evaporation and the crude product was recrystallized from an aliphatic hydrocarbon fraction boiling at 60°–80° C., to which there had been added a trace of benzene. The resulting 4-cyclohexyloxy-5,7-dinitro-2-trifluoromethylbenzimidazole product melted at 151°–2° C. Its identity was confirmed by NMR and by elemental analysis.

EXAMPLE 6

4-sec-BUTYLTHIO-5,7-DINITRO-2-TRIFLUOROMETHYLBENZIMIDAZOLE

In 200 milliliters of ethanol, 1 gram of sodium (0.04 mole) was reacted with 3.6 grams of 2-butanethiol (0.04 mole). The mixture was stirred for one-half hour. Then 4-chloro-5,7-dinitro-2-trifluoromethylbenzimidazole (6.2 grams; 0.02 mole) was added, and the resulting reaction mixture was stirred overnight, poured into water, acidified, and filtered to separate the desired 4-sec-butylthio-5,7-dinitro-2-trifluoromethylbenzimidazole. It was recrystallized twice from a mixture of benzene and an aliphatic hydrocarbon fraction boiling at 60°–80° C.., m.p., 111°–15° C.

EXAMPLE 7

4-PENTYL-5,7-DINITRO-2-TRIFLUOROMETHYLBENZIMIDAZOLE

4-Chloro-5,7-dinitro-2-trifluoromethylbenzimidazole (6.2 grams) was reacted with potassium diethyl butylmalonate (11.2 grams) in tert-butanol. The reaction mixture was warmed at 40° C. over a week-end, then poured into water. A yellow solid precipitate, the desired 4-(1,1-bis(carboethoxy)pentyl)-5,7-dinitro-2-trifluoromethylbenzimidazole. It was collected by filtration, 9.6 grams, and used directly in the subsequent reaction.

The 9.6 grams in 90 milliliters of concentrated sulfuric acid was added portionwise to 30 milliliters of stirred water. After the addition was complete, the mixture was heated to 95°–100° C. for three hours, with stirring. The reaction mixture was poured into water and ice and extracted with ethyl acetate. The ethyl acetate was removed by evaporation and the resulting 4-(1-carboxypentyl)-5,7-dinitro-2-trifluoromethylbenzimidazole, 6 grams of a brown oil, was used directly in the subsequent reaction.

To the 6 grams in 50 milliliters of dimethylformamide was added 3 grams of sodium bicarbonate. The mixture was heated to 85°–90° C. and maintained for two hours; gas was evolved. The reaction mixture was then poured into water, acidified, and extracted with ethyl acetate. The ethyl acetate was removed by evaporation and the crude product was chromatographed on 250 milliliters of silica gel, using benzene as eluant. The product fractions were combined, the benzene was removed by filtration, and the crude product was recrystallized from an aliphatic hydrocarbon fraction boiling at 60°–80° C. As a result of these operations, there was obtained the desired 4-pentyl-5,7-dinitro-2-trifluoromethylbenzimidazole, m.p. 86°–8° C.

EXAMPLE 8

4-tert-BUTYL-5,7-DINITRO-2-TRIFLUOROMETHYLBENZIMIDAZOLE 4-tert-Butyl-6-nitro-2-trifluoromethylbenzimidazole (6.0 grams of crude) was dissolved in 100 milliliters of ethanol and a small amount of platinum oxide was added. The reaction mixture was then placed in a pressure container and hydrogenated until hydrogen uptake ceased. The reaction mixture was filtered and solvent removed to yield 8.6 grams of crude 4-tert-butyl-6-amino-2-trifluoromethylbenzimidazole, as a brown oil.

This oil was mixed with 40 milliliters of 2N HCl and 40 milliliters of $H_2O$ and cooled to a temperature of 5°–10° C. To the mixture was added, portionwise, 2.4 grams of sodium nitrite in 10 milliliters of water. The reaction mixture was stirred for 15 minutes at 5°–10° C., then 35 grams of 50 percent hypophosphorous acid were added. The reaction mixture was stirred at 5°–10° C. and then stored overnight in a refrigerator.

There resulted a gummy solid. It was extracted from the aqueous material with ethyl acetate; the ethyl acetate was removed by evaporation and the resulting crude product was chromatographed on magnesium silicate using as eluant a 1:1 mixture of benzene and an aliphatic hydrocarbon fraction boiling at 60°–80° C. The desired 4-tert-butyl-2-trifluoromethylbenzimidazole, m.p., 111°–13° C., was obtained and used directly in the subsequent reaction.

To a solution of 4.0 grams of the crude 4-tert-butyl-2-trifluoromethylbenzimidazole in 80 milliliters of concentrated sulfuric acid was added 4.0 grams of potassium nitrate. During the addition the temperature of the reaction mixture rose from 18° to 28° C. After stirring overnight at 98° C. the reaction mixture was poured into 500 milliliters of ice and water. A colorless solid precipitated and was collected by filtration and air dried. The solid was recrystallized from boiling benzene, with filtration. NMR confirmed the identity of the product as the desired 4-tert-butyl-5,7-dinitro-2-trifluoromethylbenzimidazole. It melted at 149°–52° C.

Other representative products of the present invention, prepared according to the foregoing teachings and examples, are set forth in the following table.

TABLE I

[Structure: benzimidazole with NO$_2$ groups at 5,7-positions, R$^0$ substituent, N-R$^1$, and 2-CF$_2$-Y group]

| R$^0$ and R$^1$ | Y | Characterizing Property |
|---|---|---|
| H, (1,2-dimethyl-n-butyl) | F | m.p., 110–13° C. |
| H, (2-decahydronaphthyl) | F | m.p., 179–80° C. |
| H, tert-butyl | Cl | m.w., 363.7 |
| H, n-heptyl | F | m.p., 118–20° C. |
| H, (1-ethyl-1-methyl-n-propyl) | F | m.p., 140–43° C. |
| piperidino | CF$_3$ | m.w., 409.3 |
| H, (4-methylcyclohexyl) | F | m.p., 192–99° C. |
| octahydroazocino | F | m.p., 135–38° C. |
| H, (1,3-dimethyl-n-butyl) | F | m.p., 132–36° C. |
| H, (2,2,3,3,4,4,4-heptafluoro-n-butyl) | F | m.w., 425.2 |
| (decahydroisoquinolyl) | F | m.p., 218–25° C. |
| H, neopentyl | F | m.p., 181–83° C. |
| (3-azabicyclo(3.3.2)decan-3-yl) | F | m.w., 413.4 |
| H, (1,2,2-trimethyl-n-propyl) | F | m.p., 183–87° C. |
| methyl, n-propyl | F | m.p., 133–35° C. |
| isopropyl, cyclopentyl | F | m.w., 401.4 |
| cyclohexyl, cyclohexyl | F | m.p., 127–30° C. |
| n-butyl, n-butyl | F | m.p., 116–18° C. |
| H, 4-hexenyl | H | m.w., 355.3 |
| H, n-propyl | F | m.p., 134–36° C. |
| H, (1-methyl-n-butyl) | F | m.p., 143–45° C. |
| H, isobutyl | F | m.p., 138–42° C. |
| H, isopropyl | C$_2$F$_5$ | m.w., 433.3 |
| H, (4-tert-butylcyclohexyl) | F | m.p., 212–17° C. |
| H, isopropyl | F | m.p., 183–85° C. |
| methyl, (2,2-difluoroethyl) | F | m.w., 321.2 |
| methyl, cyclohexyl | F | m.p., 188–91° C. |
| H, (3-methylcyclohexyl) | F | m.p., 183–90° C. |
| H, cyclooctyl | F | m.p., 162–66° C. |
| H, (1-cyclohexylethyl) | F | m.w., 401.4 |
| isopropyl, isopropyl | F | m.p., 119–22° C. |
| H, n-octyl | F | m.p., 87–89° C. |
| H, propynyl | F | m.p., 166–70° C. |
| H, (cyclopropylmethyl) | H | m.w., 327.3 |
| H, cycloheptyl | F | m.p., 153–57° C. |
| H, (2-methylcyclohexyl) | F | m.p., 182–85° C. |
| CH$_3$, (cyclooctylmethyl) | CF$_3$ | m.w., 479.4 |
| hexahydroazepino | F | m.p., 192–95° C. |
| (3-azabicyclo(3.3.1)nonan-3-yl) | F | m.w., 399.3 |
| H, sec-butyl | F | m.p., 156–57° C. |
| H, (2,2,2-trifluoroethyl) | F | m.p., 186–89° C. |
| H, cyclopropyl | F | m.p., 201–03° C. |
| ethyl, (3-(trifluoromethyl)benzyl) | F | m.w., 477.3 |
| n-propyl, n-propyl | F | m.p., 101–03° C. |
| H, n-propyl | F | m.p., 166–70° C. |
| H, (4-methoxybenzyl) | F | m.w., 411.3 |
| H, (1,1,3,3-tetramethylbutyl) | F | m.p., 127–30° C. |
| allyl, allyl | F | m.p., 149–52° C. |
| H, (3-methylcyclopentyl) | F | m.w., 373.3 |
| H, (3-cyanobenzyl) | F | m.w., 406.3 |
| H, (cyclohexylmethyl) | F | m.p., 181–83° C. |
| H, tert-pentyl | F | m.p., 158–61° C. |
| methyl, (2-cyclohexyl-1-methylethyl) | F | m.p., 97–110° C. |
| (2-azabicyclo(3.2.1)octan-2-yl) | F | m.w., 385.3 |
| H, cyclohexyl | F | m.p., 218–21° C. |
| ethyl, n-butyl | F | m.p., 126–29° C. |
| H, 5-decynyl | F | m.w., 427.4 |
| H, (1-n-propyl-n-octyl) | F | oil |
| H, (2-norbornyl) | F | m.p., 202–05° C. |
| H, n-pentyl | F | m.p., 144–47° C. |
| H, (4-isopropylcyclooctyl) | F | m.w., 443.4 |
| H, (2-cyclopentyl-1-methylethyl) | F | m.p., 132–35° C. |
| (3-azabicyclo(3.2.2)nonan-3-yl) | F | m.p., 214–17° C. |
| H, n-hexyl | F | m.p. 120–24° C. |
| H, (2,4,5-trichlorobenzyl) | F | m.w., 484.6 |
| (1,2,3,4-tetrahydroisoquinolyl) | F | m.p., 268–70° C. (dec.) |
| (decahydroquinolyl) | F | m.p., 167–69° C. |
| H, (3-methylbenzyl) | F | m.w., 395.3 |
| methyl, (decahydronapth-2-yl) | F | m.p., 149–57° C. |
| H, 1-adamantyl | F | m.p., 245–48° C. |
| H, benzyl | F | m.p., 238–40° C. |
| H, tert-butyl | CF$_3$ | m.w., 397.3 |
| H, (1,2,2-trimethyl-n-propyl) sodium salt | F | m.w., 397.3 |
| (2-n-propylpiperidino) | F | m.p., 162–66° C. |
| H, (2,4-dinitrobenzyl) | F | m.w., 471.3 |

TABLE I-continued

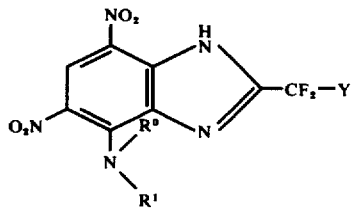

| R⁰ and R¹ | Y | Characterizing Property |
|---|---|---|
| (4-methylpiperidino) | F | m.p., 199–203° C. |
| H, ethyl | F | m.p., 183–85° C. |

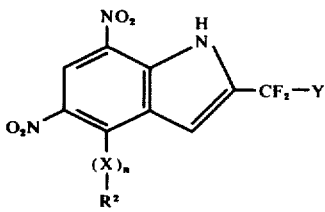

| n | X | R² | Y | Characterizing Property |
|---|---|---|---|---|
| 1 | O | methyl | F | m.p., 134–36° C. |
| 1 | O | 1-vinylbutyl | CF₃ | m.w., 424.3 |
| 1 | O | isopropyl | F | m.p., 166–68° C. |
| 1 | O | hexyl | F | m.p., 86–7° C. |
| 1 | O | cyclohexylmethyl | F | m.p., 122–25° C. |
| 1 | O | 2-norbornyl | F | m.p., 141–43.5° C. |
| 1 | O | ethyl | F | m.p., 114–18° C. |
| 1 | O | sec-butyl | F | m.p., 146–49° C. |
| 1 | O | cycloheptyl | H | m.w., 332.3 |
| 1 | O | 1-methylcyclohexyl | F | m.w., 410.3 (sodium salt) |
| 1 | O | 1,2,2-trimethylpropyl | F | m.p., 172–76° C. |
| 1 | O | 2-decahydronaphthyl | F | m.p., 119–22° C. |
| 1 | O | 1,3-dimethylbutyl | F | m.p., 91–3° C. |
| 1 | O | 4-tert-butylcyclohexyl | F | m.p., 161–64° C. |
| 1 | O | tert-butyl | F | m.w., 348.3 |
| 1 | S | methyl | Cl | m.w., 338.7 |
| 1 | S | isobutyl | F | m.p., 139–42° C. |
| 1 | S | tert-butyl | F | m.p., 148–51° C. |
| 1 | S | isopropyl | F | m.p., 159–63° C. |
| 1 | S | allyl | F | m.p., 239–41° C. |
| 1 | S | propyl | F | m.p., 127–29° C. |
| 1 | S | heptyl | F | m.p., 113–17° C. |
| 1 | S | cyclohexyl | F | m.p., 155–60° C. |
| 1 | S | cyclopentylmethyl | C₂F₅ | m.w., 490.4 |
| 0 | — | methyl | F | m.p., 128–31° C. |
| 0 | — | ethyl | Cl | m.w., 320.7 |
| 0 | — | isopentyl | F | m.p., 95–6° C. |
| 0 | — | octyl | H | m.w., 370.4 |
| 0 | — | methyl | CF₃ | m.p., 122–25° C. |
| 0 | — | 2-butenyl | F | m.w., 330.2 |
| 0 | — | methyl | C₂F₅ | m.p., 118–20.5° C. |
| 0 | — | sec-butyl | CF₃ | m.p., 89–92° C. |
| 0 | — | 1-decahydronaphthyl | CF₃ | m.w., 462.4 |
| 0 | — | 3-ethylcyclopentyl | Cl | m.w., 388.8 |

The compounds of the present invention are useful for the control of insect and arachnid pests and can be used for the control of those insect and arachnid pests found on the roots or aerial portion of plants. These compounds are active, for example, against such arachnids as red spider mite, citrus mite, two-spotted spider mite, Pacific mite, clover mite, fowl mite, various species of ticks, and various species of spiders. The compounds are also active against insects of the various orders including Mexican bean beetle, boll weevil, corn rootworm, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, white grubs, melon aphid, rose aphid, white fly, grain aphid, corn leaf aphid, pea aphid, mealybugs, scales, leafhoppers, citrus aphid, spotted alfalfa aphid, green peach aphid, bean aphid, milkweed bug, tarnished plant bug, box elder bug, bed bug, squash bug, chinch bug, house fly, yellow fever mosquito, stable fly, horn fly, cabbage maggot, carrot rust fly, Southern armyworm, codling moth, cutworm, clothes moth, Indianmeal moth, leafrollers, corn earworm, European corn borer, cabbage looper, cotton bollworm, bagworm, sod webworm, fall armyworm, German cockroach, and American cockroach.

In addition to utilization for the control of pests on plants, the compounds of this sub-genus of the present invention can also be included in inks, adhesives, soaps, polymeric materials, cutting oils or in oil or latex paints. Also, the products can be distributed in textiles, cellulose materials, or in grains, or can be employed in the impregnation of wood and lumber. Additionally, they can be applied to seeds. In yet other procedures, the products can be vaporized or sprayed or distributed as aerosols into the air, or onto surfaces in contact with the air. In such applications, the compounds manifest the useful properties hereinbefore described.

The methods of the present invention comprise contacting an insect or arachnid with an inactivating amount of one of the compounds of the present invention. Contacting can be affected by application of one or more of the products to a habitat of the insect or arachnid. Representative habitats include soil, air, water, food, vegetation, inert objects, stored matter such as grains, other animal organisms, and the like. The inactivation can be lethal, immediately, or with delay, or can be a sub-lethal one in which the inactivated insect or arachnid is rendered incapable of carrying out one or more of its normal life processes. Among known insecticides, this latter situation typically prevails when one of the systems of the organism, often the nervous system, is seriously disturbed; however, the precise mechanism by which the compounds constituting the present active agent work is not yet known, and the insecticidal and arachnicidal method of the present invention is not limited by any mode of operation.

The utilization of an inactivating amount of one of the compounds of the present invention is critical to the insecticidal and arachnicidal method of the present invention. The inactivating amount can sometimes be administered by employing the compound in unmodified form. However, for good results, it is generally necessary that the compound or compounds be employed in modified form, that is, as one component of a composition formulated to implement the arachnicidal and insecticidal effects. Thus, for example, the active agent can be mixed with water or other liquid or liquids, preferably aided by the usage of a surface active agent. The active agent can also be incorporated on a finely divided solid, which can be a surface active substance, to yield a wettable powder, which can subsequently be dispersed in water or other liquid, or incorporated as part of a dust which can be applied directly. Other methods of formulation are known in the art and can be employed in implementing the present invention.

The exact concentration of one or more of the compounds of the present invention is a composition thereof with one or a plurality of adjuvants can vary; it is necessary only that one or more of the products be present in such amount as to make possible the application of an inactivating dosage to an insect or anarchnid. In many situations, a composition comprising 0.00001 percent of the present active agent is effective for the administration of an inactivating amount thereof to insect and arachnid pest organisms. Compositions having a higher concentration of active agent, such as a concentration of from 0.00001 to 0.5 percent, can of course be employed. In still other operations, compositions containing from 0.5 to 98 percent by weight of one compound or from 0.5 to 98 percent of a total of more than one compound, are conveniently employed. Such compositions are adapted to be employed as treating compositions and applied to insects and arachnids and to their habitats, or to be employed as concentrates and subsequently diluted with additional adjuvant to produce ultimate treating compositions.

Liquid compositions containing the desired amount of active agent are prepared by dissolving the substance in an organic liquid or by dispersing the substance in water with or without the aid of a suitable surface active dispersing agent such as an ionic or non-ionic emulsifying agent. Such compositions can also contain modifying substances which serve as a "spreader" and "sticker" on plant foliage. Suitable organic liquid carriers include the agricultural spray oils and the petroleum distillates such as diesel fuel, kerosene, fuel oil napthas and Stoddard solvent. Among such liquids the petroleum distillates are generally preferred. The aqueous compositions can contain one or more water immiscible solvents for the toxicant compound. In such compositions, the carrier comprises an aqueous emulsion, e.g., a mixture of water, emulsifying agent and water immiscible solvent. The choice of dispersing and emulsifying agent and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, and the like. For a view of known surface-active agents which are suitably employed in implementing the present invention, attention is directed to U.S. Pat. No. 3,095,299, second column, lines 25–36, and references there cited.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the practices of the present invention. Also, such dust compositions can be dispersed in water, with or without the aid of a dispersing agent, to form spray mixtures.

Also, the compounds of the present invention can be employed in granular formulations. These formulations are prepared in conventional manner, typically by dissolving the compound in a solvent with or without a surface-active agent and spraying or otherwise distributing the resulting solution onto pre-formed granules. Such granular formulations are capable of providing longer-lasting activity and may be preferred for crops such as corn where repeated application is not practical.

When operating in accordance with the present invention one or more of the compounds or a composition containing one or more of the compounds is applied to the pests to be controlled directly or by means of application to a portion or portions of their habitat in any convenient manner, for example, by means of hand dusters or sprayers or by simple mixing with the food to be ingested by the organisms. Application to the foliage of plants is conveniently carried out with powder dusters, boom sprayers, and fog sprayers. In such foliar applications, the employed compositions should not contain any appreciable amounts of any phytotoxic diluents. In large-scale operations, dusts, or low-volume sprays can be applied from an airplane. The present invention also comprehends the employment of compositions comprising one or more of the compounds of the present invention, an adjuvant, and one or more biologically active materials, such as other insecticides, fungicides, miticides, bactericides, nematocides, and the like.

EXAMPLE 9

Compounds evaluated for the control of insects and arachnids, as reported in the following examples, were formulated in accordance with the following procedure. Initially, 55 grams of a mixture of two nonionic sulfonate emulsifiers were mixed with 1 liter of cyclohexanone. Of the resulting mixture, 0.9 milliliter was subsequently further mixed with 90 milligrams of the subject compound and diluted with distilled water to 90 milliliters containing the subject compound at a concentration of 1000 parts per million. For evaluation at lower concentrations, the mixture was further diluted with a dilution composition consisting of 4 liters of distilled water and a total of 1.8 milliliter of the same two nonionic sulfonate emulsifiers.

The insecticidal and arachnicidal activity of the compounds of this invention is illustrated by the following tests against representative insects and arachnids.

TEST METHODS

Mexican Bean Beetle —*Epilachna varivestis* (Coleoptera)

Cuttings of four- to six-day-old Bountiful snap bean plants containing two leaves with approximately 5 square inches of leaf surface each were placed in water. The leaves were sprayed to wetting with about 5–10 ml. of a formulation containing a predetermined level of the test compound. Half of the formulation was sprayed on the top surface and half on the bottom surface of the leaf using a DeVilbiss atomizer at 10 psi held at a distance of about 18 inches from the leaf. After the leaves had dried, they were cut from the stem and placed separately in petri dishes. Ten third instar, non-molting Mexican bean beetle larvae grown on Bountiful snap beans were placed on each leaf. Controls consisted of two leaves sprayed with 5 ml. of a 500 ppm. formulation of S-(1,2-dicarbethoxyethyl) O,O-dimethyl phosphorodithioate (reference standard), two leaves sprayed with the formulation without the active ingredient and two leaves held as untreated controls. After 48 hours, a mortality count was made and the amount of feeding noted. Moribund larvae were were counted as dead. The following toxicity rating scale was used:

| Percent Dead | Rating |
|---|---|
| 0–10 | 0 |
| 11–20 | 1 |
| 21–30 | 2 |
| 31–40 | 3 |
| 41–50 | 4 |
| 51–60 | 5 |
| 61–70 | 6 |
| 71–80 | 7 |
| 81–90 | 8 |

-continued

| Percent Dead | Rating |
|---|---|
| 91–100 | 9 |

Southern Armyworm —*Prodenia eridania* (Lepidoptera)

Ten uniform Southern armyworm larvae about 1–1.5 cm. in length, grown on Henderson lima beans, were placed on excized bean leaves in petri dishes. The bean leaves were obtained and sprayed with the insecticide in the same way as were the snap bean leaves in the Mexican bean beetle test. The reference standards in this instance were leaves sprayed with 5 ml. of 100 ppm. DDT solution. Mortality counts were made 48 hours after spraying and again moribund larvae were counted as dead. Missing larvae which had probably been eaten were considered alive. The same rating scale was used as in the Mexican bean beetle test.

Two-Spotted Spider Mite —*Tetranychus urticae* (Acarina)

Two-spotted spider mites were raised on green bean plants, then transferred to squash plants. The squash plants were maintained for two days so that the infestation was well established. The infected squash plants were then sprayed with a test formulation containing the subject compound as in the preceding test methods. Mortality was determind by estimation 48 hours after spraying. The same rating scale was used as in other test procedures.

Milkweed Bug —*Oncopelitis fasciatus* (Hemiptera)

Ten adult milkweed bugs were chilled and placed in a test cage. The cages containing the bugs were sprayed with 5 ml. of a test formulation containing a pre-determined amount of the insecticide, using a DeVilbiss atomizer at 10 psi held 33 inches from the top of the cage. After the cage had been allowed to dry the bugs were fed and watered for 48 hours. A formulation containing 500 ppm. of S-(1,2-dicarbethoxyethyl) O,O-dimethyl phosphorodithioate was used as a reference standard and two unsprayed cages were kept as controls. Mortality counts were made 48 hours after spraying. Moribund adults were considered dead. The same rating scale was employed as before.

House Fly —*Musca domestica* (Diptera)

Rearing cages containing four-day-old adult house flies were chilled at 35°–40° F. for about 1 hour. One hundred flies were transferred from the rearing cage to each test cage using a small scoop. The caged flies were kept for 1–2 hours at 70°–80° F. The cages were sprayed in the same manner as described for the milkweed bug with 5 ml. of the test formulation. Two unsprayed cages were held as controls and two cages were sprayed with a 50 ppm. DDT formulation as a reference standard. Mortality counts were made 24 hours after spraying. All flies that did not fly or did not walk up from the bottom of the cage were considered moribund. The same rating scale was employed as heretofore.

Boll Weevil —*Anthonomus grandis* (Coleoptera)

The procedure was identical to that employed for the Mexican bean beetle and the Southern armyworm, except that 10 adult boll weevils were placed on cotton leaves that had been dipped into formulations of the test compounds. The same rating scale was used.

TEST RESULTS

EXAMPLE 10

EVALUATION OF COMPOUNDS AGAINST MEXICAN BEAN BEETLE

Various compounds of the present invention were evaluated in accordance with the test method described above against Mexican Bean Beetle. The compounds so evaluated, the rates employed, and the results of the evaluations are as set forth in the following table. When more than one evaluation was carried out at a given rate, the result reported for that rate is an average of the several results.

TABLE II

| Compound | Rate in Parts Per Million | Toxicity Rating Against Mexican Bean Beetle |
|---|---|---|
| 4-(1,3-dimethyl-n-butyl-amino)-5,7-dinitro-2-trifluoromethylbenzimidazole | 500 | 9.0 |
|  | 250 | 9.0 |
|  | 100 | 9.0 |
|  | 50 | 9.0 |
|  | 25 | 8.5 |
| 4-octahydroazocino-5,7-dinitro-4-trifluoromethylbenzimidazole | 500 | 9.0 |
|  | 250 | 9.0 |
|  | 100 | 7.5 |
|  | 50 | 9.0 |
|  | 25 | 9.0 |
| 4-(1,1,3,3-tetramethylbutylamino)-5,7-dinitro-2-trifluoromethylbenzimidazole | 500 | 9.0 |
|  | 250 | 9.0 |
|  | 100 | 9.0 |
|  | 50 | 9.0 |
|  | 25 | 9.0 |
| 4-(decahydroisoquinolyl)-5,7-dinitro-2-trifluoromethylbenzimidazole | 500 | 9.0 |
|  | 250 | 8.5 |
|  | 100 | 9.0 |
|  | 50 | 9.0 |
|  | 25 | 9.0 |
| 4-(3-azabicyclo(3.2.2)nonan-3-yl)-5,7-dinitro-2-trifluoromethylbenzimidazole | 500 | 9.0 |
|  | 250 | 9.0 |
|  | 100 | 9.0 |
|  | 50 | 9.0 |
| 4-(neopentylamino)-5,7-dinitro-2-trifluoromethylbenzimidazole | 500 | 9.0 |
|  | 250 | 9.0 |
|  | 100 | 8.5 |
|  | 50 | 8.0 |
| 4-(4-methylcyclohexylamino)-5,7-dinitro-2-trifluoromethylbenzimidazole | 500 | 9.0 |
|  | 250 | 9.0 |
|  | 100 | 8.0 |
|  | 50 | 9.0 |
|  | 25 | 9.0 |
| 4-(cyclohexylmethylamino)-5,7-dinitro-2-trifluoromethylbenzimidazole | 500 | 9.0 |
|  | 250 | 9.0 |
|  | 100 | 8.5 |
|  | 50 | 9.0 |
|  | 25 | 9.0 |
| 4-(tert-pentylamino)-5,7-dinitro-2-trifluoromethylbenzimidazole | 500 | 9.0 |
|  | 250 | 8.5 |
|  | 100 | 8.0 |
|  | 50 | 7.5 |
|  | 25 | 8.5 |
| 4-(tert-butylamino)-5,7-dinitro-2-trifluoromethylbenzimidazole | 500 | 9.0 |
|  | 250 | 9.0 |
|  | 100 | 9.0 |
|  | 50 | 9.0 |
|  | 25 | 9.0 |
| 4-(2-norbornylamino)-5,7-dinitro-2-trifluoromethylbenzimidazole | 500 | 9.0 |
|  | 250 | 9.0 |
|  | 100 | 9.0 |
|  | 50 | 9.0 |
|  | 25 | 8.0 |
| 4-(2-cyclohexyl-N,1-dimethylethylamino)-5,7-dinitro-2-trifluoromethylbenzimidazole | 500 | 8.5 |
|  | 250 | 6.0 |
|  | 100 | 6.5 |
|  | 50 |  |

TABLE II-continued

| Compound | Rate in Parts Per Million | Toxicity Rating Against Mexican Bean Beetle |
|---|---|---|
| 4-(1-ethyl-1-methyl-n-propyl-amino)-5,7-dinitro-2-trifluoro-methylbenzimidazole | 500 | 9.0 |
|  | 250 | 9.0 |
|  | 100 | 8.5 |
|  | 50 | 8.0 |
|  | 25 | 9.0 |
| 4-(n-pentylamino)-5,7-dinitro-2-trifluoromethylbenzimidazole | 500 | 9.0 |
|  | 250 | 9.0 |
|  | 100 | 7.5 |
|  | 50 | 8.5 |
| 4-(n-heptylamino)-5,7-dinitro-2-trifluoromethylbenzimidazole | 500 | 8.5 |
|  | 250 | 9.0 |
|  | 100 | 8.5 |
|  | 50 | 9.0 |
|  | 25 | 8.5 |
| 4-(diallylamino)-5,7-dinitro-2-trifluoromethylbenzimidazole | 500 | 9.0 |
|  | 250 | 9.0 |
|  | 100 | 7.5 |
|  | 50 | 8.5 |
| 4-(2-cyclopentyl-1-methyl-ethylamino-5,7-dinitro-2-trifluoromethylbenzimidazole | 500 | 9.0 |
|  | 250 | 9.0 |
|  | 100 | 7.5 |
|  | 50 | 8.5 |
| 4-(1-adamantylamino)-5,7-dinitro-2-trifluoromethyl-benzimidazole | 500 | 9.0 |
|  | 250 | 9.0 |
|  | 100 | 8.0 |
|  | 50 | 8.5 |
| 4-(n-hexylamino)-5,7-dinitro-2-trifluoromethylbenzimidazole | 500 | 9.0 |
|  | 250 | 9.0 |
|  | 100 | 8.5 |
|  | 50 | 8.5 |
| 4-(benzylamino)-5,7-dinitro-2-trifluoromethylbenzimidazole | 500 | 9.0 |
|  | 250 | 9.0 |
|  | 100 | 8.5 |
| 4-piperidino-5,7-dinitro-2-trifluoromethylbenzimidazole | 500 | 9.0 |
|  | 250 | 8.5 |
|  | 100 | 8.5 |
| 4-(di-n-butylamino)-5,7-dinitro-2-trifluoromethylbenzimidazole | 500 | 9.0 |
|  | 250 | 7.5 |
|  | 100 | 8.5 |
| 4-(cyclohexylamino)-5,7-dinitro-2-trifluoromethylbenzimidazole | 500 | 9.0 |
|  | 250 | 9.0 |
|  | 100 | 9.0 |
| 4-(diisopropylamino)-5,7-dinitro-2-trifluoromethylbenzimidazole | 500 | 8.5 |
|  | 250 | 9.0 |
|  | 100 | 9.0 |
|  | 50 | 9.0 |
|  | 25 | 9.0 |
| 4-(n-octylamino)-5,7-dinitro-2-trifluoromethylbenzimidazole | 500 | 9.0 |
|  | 250 | 9.0 |
|  | 100 | 7.5 |
| 4-(dicyclohexylamino)-5,7-dinitro-2-trifluoromethylbenzimidazole | 500 | 9.0 |
|  | 250 | 9.0 |
| 4-(N-n-butylethylamino)-5,7-dinitro-2-trifluoromethylbenzimidazole | 500 | 9.0 |
|  | 250 | 9.0 |
|  | 100 | 9.0 |
|  | 50 | 9.0 |
|  | 25 | 9.0 |
| 4-(N-methyl-n-propylamino)-5,7-dinitro-2-trifluoromethyl-benzimidazole | 500 | 8.5 |
|  | 250 | 8.5 |
|  | 100 | 9.0 |
|  | 50 | 9.0 |
| 4-(1,2,2-trimethyl-n-propylamino)-5,7-dinitro-2-trifluoromethyl-benzimidazole | 500 | 9.0 |
|  | 250 | 9.0 |
|  | 100 | 9.0 |
|  | 50 | 9.0 |
|  | 25 | 8.0 |
| 4-(1,2,3,4-tetrahydroisoquin-olyl)-5,7-dinitro-2-trifluoro-methylbenzimidazole | 500 | 9.0 |
|  | 250 | 7.0 |
| 4-(decahydroquinolyl)-5,7-dinitro-2-trifluoromethyl-benzimidazole | 500 | 9.0 |
|  | 250 | 9.0 |

TABLE II-continued

| Compound | Rate in Parts Per Million | Toxicity Rating Against Mexican Bean Beetle |
|---|---|---|
| | 100 | 9.0 |
| | 50 | 9.0 |
| | 25 | 8.5 |
| 4-(N-methyldecahydronaphth-2-ylamino)-5,7-dinitro-2-trifluoromethylbenzimidazole | 500 | 9.0 |
| | 250 | 8.5 |
| | 100 | 9.0 |
| | 50 | 9.0 |
| | 25 | 8.0 |
| 4-(1,2,2-trimethyl-n-propylamino)-5,7-dinitro-2-trifluoromethylbenzimidazole, sodium salt | 500 | 9.0 |
| | 250 | 9.0 |
| | 100 | 8.5 |
| | 50 | 8.5 |
| | 25 | 9.0 |
| 4-(2-methylcyclohexylamino)-5,7-dinitro-2-trifluoromethylbenzimidazole | 500 | 8.0 |
| | 250 | 8.5 |
| | 100 | 9.0 |
| | 50 | 9.0 |
| | 25 | 9.0 |
| 4-(hexahydroazepino)-5,7-dinitro-2-trifluoromethylbenzimidazole | 500 | 9.0 |
| | 250 | 9.0 |
| | 100 | 9.0 |
| | 50 | 8.5 |
| 4-(cyclopentylamino)-5,7-dinitro-2-trifluoromethylbenzimidazole | 500 | 9.0 |
| | 250 | 9.0 |
| | 100 | 7.0 |
| | 50 | 9.0 |
| 4-(N-methylcyclohexylamino)-5,7-dinitro-2-trifluoromethylbenzimidazole | 500 | 9.0 |
| | 250 | 9.0 |
| | 100 | 7.5 |
| | 50 | 9.0 |
| 4-(3-methylcyclohexylamino)-5,7-dinitro-2-trifluoromethylbenzimidazole | 500 | 9.0 |
| | 250 | 9.0 |
| | 100 | 9.0 |
| | 50 | 8.5 |
| 4-(cyclooctylamino)-5,7-dinitro-2-trifluoromethylbenzimidazole | 500 | 9.0 |
| | 250 | 9.0 |
| | 100 | 8.0 |
| | 50 | 8.0 |
| 4-(N-(4-tert-butylcyclohexylamino)-5,7-dinitro-2-trifluoromethylbenzimidazole | 500 | 9.0 |
| | 250 | 9.0 |
| | 100 | 8.0 |
| | 50 | 9.0 |
| 4-(isobutylamino)-5,7-dinitro-2-trifluoromethylbenzimidazole | 500 | 9.0 |
| | 250 | 7.0 |
| | 100 | 8.5 |
| | 50 | 8.5 |
| | 25 | 8.5 |
| 4-(1-methyl-n-butylamino)-5,7-dinitro-2-trifluoromethylbenzimidazole | 500 | 9.0 |
| | 250 | 8.0 |
| | 100 | 9.0 |
| | 50 | 9.0 |
| | 25 | 8.5 |
| 4-(sec-butylamino)-5,7-dinitro-2-trifluoromethylbenzimidazole | 500 | 8.5 |
| | 250 | 8.5 |
| | 100 | 9.0 |
| | 50 | 9.0 |
| | 25 | 8.5 |
| 4-(2-n-propylpiperidino)-5,7-dinitro-2-trifluoromethylbenzimidazole | 500 | 9.0 |
| | 250 | 9.0 |
| | 100 | 9.0 |
| | 50 | 9.0 |
| | 25 | 8.5 |
| 4-(dodecyclamino)-5,7-dinitro-2-trifluoromethylbenzimidazole | 500 | 6.5 |
| 4-(cyclopropylamino)-5,7-dinitro-2-trifluoromethylbenzimidazole | 500 | 8.5 |
| | 250 | 8.5 |
| | 100 | 9.0 |
| | 50 | 9.0 |
| | 25 | 9.0 |
| 4-(4-methylpiperidino)-5,7-dinitro-2-trifluoromethylbenzimidazole | 500 | 9.0 |
| | 250 | 9.0 |
| | 100 | 9.0 |
| | 50 | 8.5 |
| | 25 | 8.5 |

TABLE II-continued

| Compound | Rate in Parts Per Million | Toxicity Rating Against Mexican Bean Beetle |
|---|---|---|
| 4-(1-n-pentyloctylamino)-5,7-dinitro-2-trifluoromethyl-benzimidazole | 500 | 8.0 |
| 4-(n-propylamino)-5,7-dinitro-2-trifluoromethylbenzimidazole | 250 | 7.5 |
|  | 500 | 8.5 |
|  | 250 | 9.0 |
|  | 100 | 8.5 |
|  | 50 | 8.5 |
| 4-(di-n-propylamino)-5,7-dinitro-2-trifluoromethylbenzimidazole | 500 | 7.5 |
|  | 250 | 8.0 |
|  | 100 | 9.0 |
|  | 50 | 8.0 |
| 4-(tert-butylamino)-5,7-dinitro-2-difluoromethylbenzimidazole | 500 | 9.0 |
|  | 250 | 9.0 |
|  | 100 | 9.0 |
|  | 50 | 7.5 |
| 4-(1,2-dimethyl-n-butylamino)-5,7-dinitro-2-trifluoromethylbenzimidazole | 500 | 9.0 |
|  | 250 | 9.0 |
|  | 100 | 9.0 |
|  | 50 | 9.0 |
|  | 25 | 9.0 |
| 4-isopropoxy-5,7-dinitro-2-trifluoromethylbenzimidazole | 1000 | 9.0 |
|  | 500 | 7.5 |
|  | 250 | 9.0 |
|  | 100 | 7.5 |
| 4-hexyloxy-5,7-dinitro-2-trifluoromethylbenzimidazole | 1000 | 9.0 |
|  | 500 | 8.5 |
|  | 250 | 7.0 |
|  | 100 | 7.0 |
| 4-(cyclohexylmethoxy)-5,7-dinitro-2-trifluoromethylbenzimidazole | 1000 | 9.0 |
|  | 500 | 8.5 |
|  | 250 | 8.0 |
|  | 100 | 9.0 |
|  | 50 | 8.5 |
| 4-cyclohexyloxy-5,7-dinitro-2-trifluoromethylbenzimidazole | 1000 | 9.0 |
|  | 500 | 9.0 |
|  | 250 | 8.5 |
|  | 100 | 9.0 |
| 4-sec-butoxy-5,7-dinitro-2-trifluoromethylbenzimidazole | 1000 | 9.0 |
|  | 500 | 8.0 |
| 4-(1,2,2-trimethyl-propoxy)-5,7-dinitro-2-trifluoromethyl-benzimidazole | 1000 | 9.0 |
|  | 500 | 9.0 |
|  | 250 | 9.0 |
|  | 100 | 8.5 |
|  | 50 | 9.0 |
|  | 25 | 8.5 |
|  | 10 | 8.0 |
| 4-(2-decahydronaphthyloxy)-5,7-dinitro-2-trifluoromethyl-benzimidazole | 1000 | 8.0 |
|  | 500 | 8.5 |
|  | 250 | 9.0 |
|  | 100 | 7.0 |
|  | 50 | 9.0 |
| 4-(1,3-dimethylbutoxy)-5,7-dinitro-2-trifluoromethylbenzimidazole | 1000 | 8.5 |
|  | 500 | 9.0 |
|  | 250 | 8.5 |
| 4-(4-tert-butylcyclohexyloxy)-5,7-dinitro-2-trifluoromethyl-benzimidazole | 1000 | 9.0 |
|  | 500 | 8.5 |
|  | 250 | 7.5 |
| 4-isopropylthio-5,7-dinitro-2-trifluoromethylbenzimidazole | 1000 | 8.5 |
|  | 500 | 7.0 |
|  | 250 | 6.5 |
| 4-propylthio-5,7-dinitro-2-trifluoromethylbenzimidazole | 1000 | 8.5 |
| 4-heptylthio-5,7-dinitro-2-trifluoromethylbenzimidazole | 1000 | 9.0 |
|  | 500 | 9.0 |
| 4-cyclohexylthio-5,7-dinitro-2-trifluoromethylbenzimidazole | 1000 | 9.0 |
|  | 500 | 8.0 |
|  | 250 | 8.5 |
|  | 100 | 9.0 |
|  | 50 | 8.5 |
| 4-tert-butyl-5,7-dinitro-2-trifluoromethylbenzimidazole | 1000 | 9.0 |
|  | 500 | 9.0 |
|  | 250 | 9.0 |

TABLE II-continued

| Compound | Rate in Parts Per Million | Toxicity Rating Against Mexican Bean Beetle |
|---|---|---|
| | 100 | 9.0 |
| | 50 | 7.0 |
| | 25 | 9.0 |
| | 10 | 9.0 |
| | 5 | 9.0 |
| 4-methyl-5,7-dinitro-2-trifluoromethylbenzimidazole | 1000 | 8.0 |
| | 500 | 7.5 |
| | 250 | 8.5 |
| 4-pentyl-5,7-dinitro-2-trifluoromethylbenzimidazole | 1000 | 9.0 |
| | 500 | 9.0 |
| | 250 | 9.0 |
| | 100 | 8.0 |
| 4-isopentyl-5,7-dinitro-2-trifluoromethylbenzimidazole | 1000 | 9.0 |
| | 500 | 9.0 |
| | 250 | 8.0 |
| | 100 | 8.0 |
| 4-methyl-5,7-dinitro-2-pentafluoroethylbenzimidazole | 1000 | 5.0 |
| | 500 | 8.5 |
| | 250 | 8.0 |
| | 100 | 7.5 |
| 4-methyl-5,7-dinitro-2-heptafluoropropylbenzimidazole | 1000 | 9.0 |
| | 500 | 8.5 |
| 4-sec-butyl-5,7-dinitro-2-pentafluoroethylbenzimidazole | 1000 | 9.0 |
| | 500 | 9.0 |
| | 250 | 9.0 |
| | 100 | 6.5 |

EXAMPLE 11

EVALUATION OF COMPOUNDS AGAINST SOUTHERN ARMYWORM

Various compounds of the present invention were evaluated in accordance with the test method above against Southern armyworm. The compounds so evaluated, the rates employed, and the results of the evaluation are as set forth in the following table. Where more than one evaluation was carried out at a given rate, the result reported for that rate is an average of the several results.

TABLE III

| Compound | Rate in Parts Per Million | Toxicity Rating Against Southern Armyworm |
|---|---|---|
| 4-(1,1,3,3-tetramethylbutyl-amino)-5,7-dinitro-2-trifluoromethylbenzimidazole | 500 | 9.0 |
| | 250 | 8.0 |
| | 100 | 8.5 |
| 4-(decahydroisoquinolyl)-5,7-dinitro-2-trifluoromethyl-benzimidazole | 500 | 9.0 |
| | 250 | 9.0 |
| 4-(4-methylcyclohexylamino)-5,7-dinitro-2-trifluoromethyl-benzimidazole | 500 | 9.0 |
| | 250 | 8.5 |
| 4-(cyclohexylmethylamino)-5,7-dinitro-2-trifluoromethyl-benzimidazole | 500 | 9.0 |
| | 250 | 8.5 |
| | 100 | 7.5 |
| 4-(tert-pentylamino)-5,7-dinitro-2-trifluoromethylbenzimidazole | 500 | 9.0 |
| | 250 | 9.0 |
| | 100 | 7.0 |
| | 50 | 6.5 |
| 4-(tert-butylamino)-5,7-dinitro-2-trifluoromethylbenzimidazole | 500 | 9.0 |
| | 250 | 8.5 |
| | 100 | 8.5 |
| 4-(1-ethyl-1-methyl-n-propyl-amino)-5,7-dinitro-2-trifluoromethylbenzimidazole | 500 | 9.0 |
| | 250 | 8.5 |
| | 100 | 8.0 |
| 4-(n-pentylamino)-5,7-dinitro-2-trifluoromethylbenzimidazole | 500 | 9.0 |
| | 250 | 8.0 |
| 4-(2-cyclopentyl-1-methylethyl-amino)-5,7-dinitro-2-trifluoromethylbenzimidazole | 500 | 8.5 |
| | 250 | 8.5 |
| 4-(1-adamantylamino)-5,7-dinitro-2-trifluoromethylbenzimidazole | 500 | 9.0 |
| | 250 | 9.0 |
| | 100 | 8.0 |
| 4-piperidino-5,7-dinitro-2- | 500 | 9.0 |

TABLE III-continued

| Compound | Rate in Parts Per Million | Toxicity Rating Against Southern Armyworm |
|---|---|---|
| trifluoromethylbenzimidazole | | |
| 4-(cyclohexylamino)-5,7-dinitro-2-trifluoromethylbenzimidazole | 250 | 8.0 |
| | 500 | 9.0 |
| 4-(1,2,2-trimethyl-n-propylamino)-5,7-dinitro-2-trifluoromethyl-benzimidazole | 250 | 8.0 |
| | 500 | 9.0 |
| | 250 | 9.0 |
| 4-(cyclooctylamino)-5,7-dinitro-2-trifluoromethylbenzimidazole | 100 | 8.5 |
| | 500 | 9.0 |
| 4-(1-methyl-n-butylamino)-5,7-dinitro-2-trifluoromethylbenzimidazole | 250 | 8.5 |
| | 500 | 9.0 |
| | 250 | 9.0 |
| 4-(di-n-propylamino)-5,7-dinitro-2-trifluoromethylbenzimidazole | 100 | 7.0 |
| | 500 | 8.5 |
| | 250 | 9.0 |
| 4-hexyloxy-5,7-dinitro-2-trifluoromethylbenzimidazole | 100 | 9.0 |
| | 1000 | 8.0 |
| 4-cyclohexylmethoxy-5,7-dinitro-2-trifluoromethylbenzimidazole | 1000 | 9.0 |
| 4-cyclohexyloxy-5,7-dinitro-2-trifluoromethylbenzimidazole | 1000 | 8.5 |
| 4-(2-norbornyloxy)-5,7-dinitro-2-trifluoromethylbenzimidazole | 1000 | 9.0 |
| 4-tert-butyl-5,7-dinitro-2-trifluoromethylbenzimidazole | 1000 | 9.0 |
| | 500 | 7.0 |
| 4-sec-butyl-5,7-dinitro-2-trifluoromethylbenzimidazole | 250 | 9.0 |
| | 1000 | 9.0 |
| | 500 | 9.0 |

EXAMPLE 12

EVALUATION OF COMPOUNDS AGAINST TWO-SPOTTED SPIDER MITE

Various compounds of the present invention were evaluated in accordance with the test method described above against two-spotted spider mite. The compounds so evaluated, the rates employed, and the results of the evaluation are as set forth in the following table.

TABLE IV

| Compound | Rate in Parts Per Million | Toxicity Rating Against Two-spotted Spider Mite |
|---|---|---|
| 4-(diisopropylamino)-5,7-dinitro-2-trifluoromethyl-benzimidazole | 500 | 9.0 |
| | 250 | 9.0 |
| | 100 | 8.5 |
| | 50 | 7.0 |
| 4-(1,2,2-trimethyl-n-propyl-amino)-5,7-dinitro-2-trifluoromethylbenzimidazole | 500 | 9.0 |
| | 250 | 8.0 |
| | 100 | 8.5 |
| | 50 | 8.0 |
| 4-(1,2,2-trimethyl-n-propyl-amino)-5,7-dinitro-2-trifluoromethylbenzimidazole, sodium salt | 500 | 9.0 |
| | 250 | 8.5 |
| | 100 | 8.0 |
| | 50 | 7.0 |
| | 25 | 8.0 |
| 4-methoxy-5,7-dinitro-2-trifluoromethylbenzimidazole | 1000 | 8.5 |
| | 500 | 7.0 |
| | 250 | 7.0 |
| 4-isopropoxy-5,7-dinitro-2-trifluoromethylbenzimidazole | 1000 | 9.0 |
| | 500 | 8.0 |
| | 250 | 9.0 |
| | 100 | 9.0 |
| | 50 | 8.5 |
| | 25 | 8.5 |
| 4-(2-norbornyloxy)-5,7-dinitro-2-trifluoromethyl-benzimidazole | 1000 | 9.0 |
| | 500 | 8.5 |
| | 250 | 8.0 |
| | 100 | 7.0 |
| 4-ethoxy-5,7-dinitro-2-trifluoromethylbenzimidazole | 1000 | 9.0 |
| | 500 | 9.0 |
| | 250 | 9.0 |

TABLE IV-continued

| Compound | Rate in Parts Per Million | Toxicity Rating Against Two-spotted Spider Mite |
|---|---|---|
| 4-sec-butoxy-5,7-dinitro-2-trifluoromethylbenzimidazole | 1000 | 9.0 |
| | 500 | 9.0 |
| | 250 | 7.5 |
| 4-(1,2,2-trimethylpropoxy)-5,7-dinitro-2-trifluoromethylbenzimidazole | 1000 | 9.0 |
| | 500 | 9.0 |
| | 250 | 7.5 |
| | 100 | 8.0 |
| | 50 | 9.0 |
| 4-heptylthio-5,7-dinitro-2-trifluoromethylbenzimidazole | 1000 | 9.0 |
| | 500 | 7.5 |
| 4-tert-butyl-5,7-dinitro-2-trifluoromethylbenzimidazole | 1000 | 9.0 |
| | 500 | 9.0 |
| | 250 | 9.0 |
| | 100 | 9.0 |
| | 50 | 9.0 |
| | 25 | 9.0 |
| 4-methyl-5,7-dinitro-2-trifluoromethylbenzimidazole | 1000 | 9.0 |
| | 500 | 9.0 |
| | 250 | 9.0 |
| 4-pentyl-5,7-dinitro-2-trifluoromethylbenzimidazole | 1000 | 9.0 |
| | 500 | 8.0 |
| | 250 | 6.0 |
| 4-methyl-5,7-dinitro-2-pentafluoroethylbenzimidazole | 1000 | 9.0 |
| | 500 | 9.0 |
| | 250 | 9.0 |
| | 100 | 9.0 |
| | 50 | 9.0 |
| | 25 | 8.5 |
| 4-methyl-5,7-dinitro-2-heptafluoropropylbenzimidazole | 1000 | 9.0 |
| | 500 | 9.0 |
| | 250 | 9.0 |
| | 100 | 9.0 |
| | 50 | 9.0 |
| | 25 | 8.5 |
| 4-sec-butyl-5,7-dinitro-2-pentafluoroethylbenzimidazole | 1000 | 9.0 |
| | 500 | 9.0 |
| | 250 | 9.0 |
| | 100 | 9.0 |
| | 50 | 9.0 |
| | 25 | 9.0 |

EXAMPLE 13

EVALUATION OF COMPOUNDS AGAINST MILKWEED BUG

Various compounds of the present invention were evaluated in accordance with the test described above against Milkweed Bug. The compounds so evaluated, the rates employed and the results of the evaluation are as set forth in the following table.

TABLE V

| Compound | Rate in Parts Per Million | Toxicity Rating Against Milkweed Bug |
|---|---|---|
| 4-(neopentylamino)-5,7-dinitro-2-trifluoromethylbenzimidazole | 500 | 9.0 |
| | 250 | 9.0 |
| 4-(1-ethyl-1-methyl-n-propylamino)-5,7-dinitro-2-trifluoromethylbenzimidazole | 500 | 9.0 |
| | 250 | 7.0 |
| | 100 | 8.0 |
| 4-(diisopropylamino)-5,7-dinitro-2-trifluoromethylbenzimidazole | 500 | 9.0 |
| | 250 | 9.0 |
| | 100 | 9.0 |
| 4-(dicyclohexylamino)-5,7-dinitro-2-trifluoromethylbenzimidazole | 500 | 9.0 |
| | 250 | 9.0 |
| | 100 | 9.0 |
| 4-(1,2,2-trimethyl-n-propylamino)-5,7-dinitro-2-trifluoromethylbenzimidazole | 500 | 9.0 |
| | 250 | 9.0 |
| | 100 | 8.5 |
| | 50 | 7.0 |
| 4-(decahydroquinolyl)-5,7- | 500 | 8.0 |

TABLE V-continued

| Compound | Rate in Parts Per Million | Toxicity Rating Against Milkweed Bug |
|---|---|---|
| dinitro-2-trifluoromethyl-benzimidazole | 250 | 8.5 |
| | 100 | 8.5 |
| | 50 | 8.0 |
| 4-(2-propynylamino)-5,7-dinitro-2-trifluoromethyl-benzimidazole | 500 | 9.0 |
| | 250 | 8.5 |
| 4-(sec-butylamino)-5,7-dinitro-2-trifluoromethyl-benzimidazole | 500 | 9.0 |
| | 250 | 8.5 |
| 4-methoxy-5,7-dinitro-2-trifluoromethylbenzimidazole | 1000 | 9.0 |
| | 500 | 9.0 |
| 4-isopropoxy-5,7-dinitro-2-trifluoromethylbenzimidazole | 250 | 7.5 |
| | 1000 | 9.0 |
| | 500 | 9.0 |
| 4-hexyloxy-5,7-dinitro-2-trifluoromethylbenzimidazole | 250 | 8.0 |
| | 1000 | 9.0 |
| 4-ethoxy-5,7-dinitro-2-trifluoromethylbenzimidazole | 500 | 9.0 |
| | 1000 | 9.0 |
| 4-sec-butoxy-5,7-dinitro-2-trifluoromethylbenzimidazole | 500 | 9.0 |
| | 1000 | 9.0 |
| | 500 | 9.0 |
| 4-(1,3-dimethylbutoxy)-5,7-dinitro-2-trifluoromethyl-benzimidazole | 250 | 8.5 |
| | 1000 | 9.0 |
| | 500 | 9.0 |
| | 250 | 6.5 |
| 4-(4-tert-butylcyclohexyloxy)-5,7-dinitro-2-trifluoromethyl-benzimidazole | 100 | 7.5 |
| | 1000 | 9.0 |
| | 500 | 9.0 |
| 4-sec-butylthio-5,7-dinitro-2-trifluoromethylbenzimidazole | 250 | 8.5 |
| | 1000 | 9.0 |
| 4-tert-butyl-5,7-dinitro-2-trifluoromethylbenzimidazole | 500 | 8.5 |
| | 1000 | 9.0 |
| | 500 | 9.0 |
| | 250 | 9.0 |
| 4-methyl-5,7-dinitro-2-pentafluoroethylbenzimidazole | 100 | 9.0 |
| | 1000 | 9.0 |
| | 500 | 8.0 |
| 4-methyl-5,7-dinitro-2-heptafluoropropylbenzimidazole | 250 | 6.0 |
| | 1000 | 9.0 |
| 4-sec-butyl-5,7-dinitro-2-pentafluoroethylbenzimidazole | 500 | 9.0 |
| | 1000 | 9.0 |
| | 500 | 9.0 |
| | 250 | 9.0 |

EXAMPLE 14

EVALUATION OF COMPOUNDS AGAINST HOUSE FLY

Various compounds of the present invention were evaluated in accordance with the test method described above against House fly. The compounds so evaluated, the rates employed, and the results of the evaluations are as set forth in the following table. Where more than one evaluation was carried out, the result reported for that rate is an average of the several results.

TABLE VI

| Compound | Rate in Parts Per Million | Toxicity Rating Against House Fly |
|---|---|---|
| 4-(tert-butylamino)-5,7-dinitro-2-trifluoromethylbenzimidazole | 500 | 9.0 |
| | 250 | 9.0 |
| | 100 | 9.0 |
| 4-(tert-butylamino)-5,7-dinitro-2-difluoromethylbenzimidazole | 500 | 9.0 |
| | 250 | 9.0 |
| | 100 | 9.0 |
| | 50 | 7.5 |
| 4-(2,2,2-trifluoroethylamino)-5,7-dinitro-2-trifluoromethyl-benzimidazole | 500 | 9.0 |
| | 250 | 9.0 |
| | 100 | 9.0 |
| | 50 | 9.0 |
| 4-(1-ethyl-1-methyl-n-propylamino)-5,7-dinitro-2-trifluoromethyl- | 500 | 8.5 |

TABLE VI-continued

| Compound | Rate in Parts Per Million | Toxicity Rating Against House Fly |
|---|---|---|
| benzimidazole | 250 | 8.5 |
| 4-(diisopropylamino)-5,7-dinitro-2-trifluoromethylbenzimidazole | 500 | 9.0 |
|  | 250 | 9.0 |
| 4-(ethylamino)-5,7-dinitro-2-trifluoromethylbenzimidazole | 500 | 9.0 |
|  | 250 | 8.5 |
|  | 100 | 8.0 |
| 4-(dicyclohexylamino)-5,7-dinitro-2-trifluoromethyl-benzimidazole | 500 | 9.0 |
|  | 250 | 9.0 |
| 4-(decahydroquinolyl)-5,7-dinitro-2-trifluoromethyl-benzimidazole | 500 | 9.0 |
|  | 250 | 8.5 |
|  | 100 | 7.5 |
| 4-(1,2,2-trimethyl-n-propylamino)-5,7-dinitro-2-trifluoromethylbenzimidazole, sodium salt | 500 | 9.0 |
|  | 250 | 9.0 |
|  | 100 | 7.5 |
|  | 50 | 9.0 |
|  | 25 | 8.0 |
| 4-(2-n-propylpiperidino)-5,7-dinitro-2-trifluoromethyl-benzimidazole | 500 | 9.0 |
|  | 250 | 9.0 |
|  | 100 | 9.0 |
|  | 50 | 9.0 |
|  | 25 | 8.5 |
| 4-(cyclopropylamino)-5,7-dinitro-2-trifluoromethylbenzimidazole | 500 | 9.0 |
|  | 250 | 9.0 |
|  | 100 | 9.0 |
|  | 50 | 7.0 |
| 4-methoxy-5,7-dinitro-2-trifluoromethylbenzimidazole | 1000 | 9.0 |
|  | 500 | 8.0 |
| 4-isopropoxy-5,7-dinitro-2-trifluoromethylbenzimidazole | 1000 | 9.0 |
|  | 500 | 9.0 |
|  | 250 | 9.0 |
|  | 100 | 9.0 |
|  | 50 | 9.0 |
|  | 25 | 8.0 |
|  | 10 | 7.5 |
| 4-hexyloxy-5,7-dinitro-2-trifluoromethylbenzimidazole | 1000 | 8.0 |
|  | 500 | 9.0 |
| 4-ethoxy-5,7-dinitro-2-trifluoromethylbenzimidazole | 1000 | 9.0 |
|  | 500 | 8.0 |
|  | 250 | 7.0 |
|  | 100 | 7.0 |
| 4-sec-butoxy-5,7-dinitro-2-trifluoromethylbenzimidazole | 1000 | 9.0 |
|  | 500 | 8.5 |
| 4-heptylthio-5,7-dinitro-2-trifluoromethylbenzimidazole | 1000 | 8.5 |
|  | 500 | 8.5 |
|  | 250 | 7.0 |
| 4-cyclohexylthio-5,7-dinitro-2-trifluoromethylbenzimidazole | 1000 | 9.0 |
|  | 500 | 9.0 |
|  | 250 | 7.5 |
| 4-tert-butyl-5,7-dinitro-2-trifluoromethylbenzimidazole | 1000 | 9.0 |
|  | 500 | 9.0 |
|  | 250 | 9.0 |
| 4-methyl-5,7-dinitro-2-heptafluoropropylbenzimidazole | 1000 | 8.5 |
|  | 500 | 9.0 |
|  | 250 | 9.0 |
|  | 100 | 9.0 |
|  | 50 | 7.5 |
| 4-sec-butyl-5,7-dinitro-2-pentafluoroethylbenzimidazole | 1000 | 9.0 |
|  | 500 | 9.0 |
|  | 250 | 9.0 |
|  | 100 | 9.0 |
|  | 50 | 7.0 |

EXAMPLE 15
EVALUATION OF COMPOUNDS AGAINST BOLL WEEVIL

Various compounds of the present invention were evaluated in accordance with the test method described above against Boll Weevil. The compounds so evaluated, the rates employed, and the results of the evaluations are as set forth in the following table. Where more than one evaluation was carried out, the result reported for that rate is an average of the several results.

TABLE VII

| Compound | Rate in Parts Per Million | Toxicity Rating Against Boll Weevil |
|---|---|---|
| 4-(1,1,3,3-tetramethylbutylamino)-5,7-dinitro-2-trifluoromethylbenzimidazole | 500 | 9.0 |
|  | 250 | 7.5 |
|  | 100 | 8.0 |
|  | 50 | 7.0 |
| 4-(neopentylamino)-5,7-dinitro-2-trifluoromethylbenzimidazole | 500 | 9.0 |
|  | 250 | 9.0 |
|  | 100 | 7.5 |
| 4-(tert-butylamino)-5,7-dinitro-2-trifluoromethylbenzimidazole | 500 | 9.0 |
|  | 250 | 9.0 |
|  | 100 | 9.0 |
|  | 50 | 9.0 |
|  | 25 | 8.5 |
| 4-(2-propynylamino)-5,7-dinitro-2-trifluoromethylbenzimidazole | 500 | 6.0 |
|  | 250 | 9.0 |
|  | 100 | 8.5 |
| 4-(1-ethyl-1-methyl-n-propylamino)-5,7-dinitro-2-trifluoromethylbenzimidazole | 500 | 8.5 |
|  | 250 | 8.5 |
|  | 100 | 8.5 |
|  | 50 | 7.5 |
| 4-(1,2,2-trimethyl-n-propylamino)-5,7-dinitro-2-trifluoromethylbenzimidazole, sodium salt | 500 | 8.5 |
|  | 250 | 9.0 |
|  | 100 | 8.5 |
|  | 50 | 8.0 |
|  | 25 | 9.0 |
| 4-(sec-butylamino)-5,7-dinitro-2-trifluoromethylbenzimidazole | 500 | 9.0 |
|  | 250 | 8.0 |
|  | 100 | 6.5 |
|  | 50 | 8.0 |
|  | 25 | 8.0 |
| 4-(dodecylamino)-5,7-dinitro-2-trifluoromethylbenzimidazole | 500 | 8.0 |
|  | 250 | 9.0 |
|  | 100 | 9.0 |
| 4-(cyclopropylamino)-5,7-dinitro-2-trifluoromethylbenzimidazole | 500 | 9.0 |
|  | 250 | 8.5 |
|  | 100 | 9.0 |
|  | 50 | 7.5 |
| 4-isopropoxy-5,7-dinitro-2-trifluoromethylbenzimidazole | 1000 | 9.0 |
|  | 500 | 9.0 |
|  | 250 | 9.0 |
|  | 100 | 9.0 |
|  | 50 | 8.5 |
|  | 25 | 9.0 |
| 4-ethoxy-5,7-dinitro-2-trifluoromethylbenzimidazole | 1000 | 8.0 |
|  | 500 | 9.0 |
|  | 250 | 8.0 |
|  | 100 | 9.0 |
|  | 50 | 8.0 |
| 4-sec-butoxy-5,7-dinitro-2-trifluoromethylbenzimidazole | 1000 | 9.0 |
|  | 500 | 9.0 |
|  | 250 | 9.0 |
|  | 100 | 7.0 |
| 4-(1,2,2-trimethylpropoxy)-5,7-dinitro-2-trifluoromethylbenzimidazole | 1000 | 8.0 |
|  | 500 | 9.0 |
|  | 250 | 9.0 |
|  | 100 | 8.5 |
|  | 50 | 9.0 |
|  | 25 | 8.5 |
| 4-tert-butyl-5,7-dinitro-2-trifluoromethylbenzimidazole | 1000 | 9.0 |
|  | 500 | 9.0 |
|  | 250 | 9.0 |
|  | 100 | 9.0 |
|  | 50 | 9.0 |
|  | 25 | 9.0 |

TABLE VII-continued

| Compound | Rate in Parts Per Million | Toxicity Rating Against Boll Weevil |
|---|---|---|
| | 10 | 9.0 |

In addition to arachnicidal and insecticidal activity, a number of the compounds of the present invention exhibit nematocidal activity. A compound which exhibits this activity to a marked degree is 4-tert-butyl-/amino-5,7-dinitro-2-trifluoromethylbenzimidazole. In employing this or other compounds of the present invention for nematocidal purposes, a nematocidal dose of the compound or compounds is distributed in soil. In general, good results are obtained with distribution rates of from 1 or less to 10 or more pounds per acre, and through such a cross-section of the soil as to provide for the presence therein of a nematocidal concentration of the active compound or compounds. Unmodified compound can be used; however, as in the instance of the arachnicidal and insecticidal activity, it is generally preferred to employ a composition comprising the active substance and one or more adjuvants such as surface-active dispersing agents, inert finely divided solids, liquids, and the like.

In representative operations, 4-(tert-butylamino)-5,7-dinitro-2-trifluoromethylbenzimidazole was evaluated for activity against root knot nematode (*Meloidogyne incognita acrita*). For these evaluations, the compound was formulated in standard procedures.

One hundred grams of dry, unsterile, sandy soil were placed in each of several jars and the soil in each jar inoculated with 5 ml. of nematode-larvae suspension. An indentation was made in the soil in each jar, and 3 grams of diatomaceous silica (Celatom MP-78) granules were placed in each. These granules were then impregnated with two milliliters of test solution containing the 4-(tert-butylamino)-5,7-dinitro-2-trifluoromethylbenzimidazole in a concentration equivalent to 20, 10, 5, or 2.5 lbs./acre (calculated on a broadcast basis). The jars were first hand shaken for a few seconds and then placed on a roller for several minutes to thoroughly incorporate the inoculum and test chemical.

The treated nematode-infested soil was then transferred to 2.5-inch plastic pots, planted to several cucumber seeds, and covered to a depth of one-half inch. The pots were then taken to a greenhouse bench where they were placed inside 2.5-inch clay pots embedded in sand. The bench received bottom heat and supplemental lighting from time controlled fluorescent lights. The greenhouse temperature was set at 78° F. All pots were watered as necessary. Duration of test was 21 days. At the end of the 21 days, the plants were observed to determine the disease rating, on a scale of 1–5 with 1 = severe disease and 5 = no disease. The results were as follows:

| Pounds/Acre | Disease Rating |
|---|---|
| 20 | 5 |
| 10 | 4 |
| 5 | 4 |
| 2.5 | 4 |

Slight chlorosis was observed in the plants treated with 5 and 2.5 pounds per acre.

In another evaluation, 4-(tert-butylamino)-5,7-dinitro-2-trifluoromethylbenzimidazole was tested against stem nematode (*Ditylenchus dipsaci*).

One hundred twenty-five grams of dry, unsterile sand was placed in each of a number of 2.5-inch plastic pots and each pot planted with 25 seeds of alfalfa var. DuPuits. The pots were inoculated by applying a 10-milliliter suspension of nematodes over each and then covering each pot immediately with 25 grams of sand. The 4-(tert-butylamino)-5,7-dinitro-2-trifluoromethylbenzimidazole, formulated in conventional liquid formulations varying only in concentration of the compound, was applied to each pot as a surface drench treatment. This treatment provided application rates equivalent to 20, 10, or 5 lbs./acre calculated on a broadcast basis.

All pots were taken to the greenhouse and placed on a cart for the duration of the test, 7–10 days. At the end of this period, all plants were evaluated for the presence of disease symptoms using a disease rating scale of 1 = severe, to 5 = no disease. The results were as follows:

| Pounds/Acre | Disease Rating |
|---|---|
| 20 | 4 |
| 10 | 4 |
| 5 | 4 |

No phytotoxicity was noted.

In addition to insecticidal activity, the compounds of Formula II exhibit herbicidal activity. Thus, in employing these compounds as insecticides for the control of insects which attack plants, due regard should be paid to the selection of rates, the growth stage of plants, the susceptibility of the plants to the compounds, and the like, in order that the insecticidal effect be achieved with little or no undesired herbicidal effect. When it is desired to utilize the herbicidal activity of the compounds, the compounds can be employed to control plant growth generally, or selectively to control weeds growing in crop plants. The compounds exhibit herbicidal activity at rates of from one-half lb. or less to 10 lbs. or more. Compounds preferred for their herbicidal activity are those wherein $n$ represents O and $R^2$ represents alkyl, especially loweralkyl of $C_1$ to $C_4$; and those wherein $n$ represents 1, X represents oxygen, and $R^2$ likewise represents alkyl.

When employed as herbicides, the compounds are conveniently formulated with adjuvants. Reference is made to the discussion hereinabove regarding the formulation of the compounds incident to utilization as insecticides. The compounds can be applied pre-emergent or post-emergent, in accordance with conventional modes of application.

Representative compounds were evaluated for herbicidal activity. Uniformly the evaluation was conducted by dispersing the respective compound with suitable surface-active agents in an aqueous solution and spraying the solution onto plots seeded with various species. A control plot was sprayed with an aqueous solution containing only the surface-active agents, in the same concentration. The plots were held under good growing conditions for twelve to thirteen days and then examined.

When evaluated by this method at a rate of 8 pounds/acre, 4-sec-butoxy-5,7-dinitro-2-trifluoromethylbenzimidazole gave essentially complete control of crabgrass, pigweed, and foxtail, without any phytotoxic effect on corn. 4-(1,2,2-Trimethylpropoxy)-5,7-dinitro-2-trifluoromethylbenzimidazole at 8 pounds/acre likewise gave good or essentially complete control of the same named weed species, without phytotoxicity to corn. Results essentially the same as these latter results were also observed with 4-isopropoxy-5,7-dinitro-2-trifluoromethylbenzimidazole at 8 pounds/acre, except that modest phytotoxicity was noted on corn. However, no phytotoxicity was noted for either cotton or soybeans.

Also, each of 4-tert-butyl-5,7-dinitro-2-trifluoromethylbenzimidazole and 4-cyclohexylthio-5,7-dinitro-2-trifluoromethylbenzimidazole was evaluated in the procedure described above at a rate of 8 pounds/acre. The former gave complete control of crabgrass, pigweed, and foxtail, with no phytotoxicity to corn or soybeans and only minor phytotoxicity to cotton. The latter compound had no phytotoxic effect on corn, cotton or soybeans, and gave good control of crabgrass and pigweed.

Those starting materials to be employed in accordance with the present invention which are of the formula:

are prepared in known procedures by nitration of corresponding compounds of the formula:

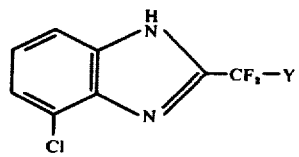

These compounds, are, in turn, prepared by reacting 3-chloro-o-phenylenediamine:

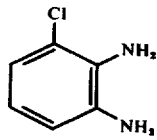

with an α,α-difluoroalkanoic acid of the formula:

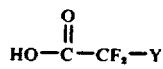

In representative operations, 40 milliliters of trifluoroacetic acid were added to a mixture of 7.4 g. of 3-chloro-o-phenylenediamine in about 200–250 milliliters of water containing 60 milliliters of concentrated HCl. The mixture was refluxed with stirring for 5 hours and then poured into water and made strongly basic with $NH_4OH$. The resulting mixture was filtered and neutralized with concentrated HCl. The product precipitated as a slowly solidifying oil, and the solid was collected by filtration, washed with water, and dried in a vacuum desiccator. The crude product consisted of brownish needles. This crude product and a second crop were chromatographed on a column of 200 milliliters of silica gel with benzene as eluant. On evaporation of the benzene, a yellow-white crystalline solid was found. This was recrystallized from benzene, m.p., 158°–159° C.

To a solution of 15 g. of the 4-chloro-2-trifluoromethylbenzimidazole in 300 milliliters of sulfuric acid there was added 70 g. of potassium nitrate (10-fold excess), keeping the temperature below 25°. The reaction mixture was then heated slowly to 110° and held there for 18 hours. After cooling, the reaction mixture was poured into one liter of ice and water to precipitate a colorless solid. The solid was washed well with water, dried under vacuum, and recrystallized from benzene to give 15.8 g. of large, colorless needles, m.p., 189°–92° C.

The foregoing nitration procedure is preferably modified for compounds wherein Y is chlorine. Since this chlorine atom is susceptible to oxidation, the reaction is preferably conducted under strong nitrating conditions—for example, fuming nitric acid—and at lower temperatures, such as temperatures below 30° C., to preclude oxidation.

The amines to be employed as starting materials in accordance with the present invention are prepared in accordance with known synthetic procedures, and many of them are known compounds. Similarly, the alcohols and mercaptans to be employed in the synthesis of compounds of Formula II are generally known compounds, and all are prepared in accordance with known synthetic procedures.

The compounds to be employed as starting materials in the preparation of compounds of Formula II wherein n represents O are in some instances known compounds. For example, 3-methyl-o-phenylenediamine is readily available for utilization in the first synthetic method. Those starting materials to be employed in the second synthetic method:

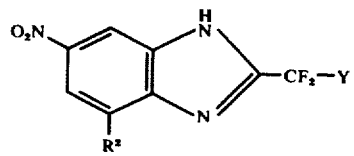

are prepared by reacting an o-phenylenediamine of the formula

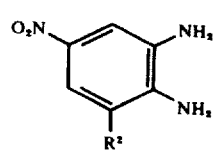

with an acid of the formula

Y—CF₂—COOH, conveniently in an inert liquid as reaction medium. The reaction proceeds readily at temperatures ranging from room temperature to 150° C. or higher, but is preferably and conveniently conducted at reflux temperatures. Some of the desired product is obtained when employing the reactants in any amount; but higher yields of product are obtained by employing equimolecular amounts or an excess of the acid, such as a one-to-ten-or-more fold excess. Water is produced as byproduct. Separation and purification are carried out in conventional procedures.

The benzimidazole starting materials for the third synthetic route are the same as those utilized in the preparation of the compounds of Formula I, the preparation of which is described above. The malonate salts to be employed in this same synthetic route are derived from the corresponding compounds of the formula R³—CH(COOEt)₂, which are in turn prepared from the simple malonate (CH₂—(COOEt)₂) and a halide R³X, in conventional procedures.

I claim:

1. An insecticidal and arachnicidal composition comprising a surface-active agent and an insecticidally or arachnicidally-effective amount of a compound of the formula

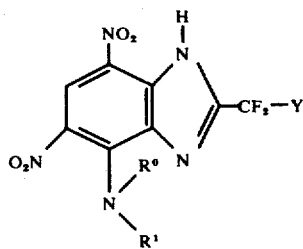

wherein Y represents
  a. hydrogen,
  b. chlorine,
  c. fluorine,
  d. trifluoromethyl, or
  e. pentafluoroethyl;
wherein
  a. when each of R⁰ and R¹ is taken separately, each independently represents, subject to the limitation that at least one of R⁰ and R¹ contains more than 1 carbon atom and that R⁰ and R¹ together contain less than 14 carbon atoms:
    1. hydrogen,
    2. alkyl,
    3. alkenyl containing more than 2 carbon atoms,
    4. alkynyl containing more than 2 carbon atoms,
    5. (fluoroalkyl)methyl wherein alkyl is C₁–C₇, both inclusive, and bears at least one fluorine atom,
    6. cycloalkyl of C₃–C₈, both inclusive,
    7. cycloalkylloweralkyl, wherein cycloalkyl is from C₃–C₈, both inclusive, and loweralkyl is from C₁–C₄, both inclusive,
    8. loweralkylcycloalkyl wherein cycloalkyl and loweralkyl are as defined in the preceding candidate moiety,
    9. adamantyl,
    10. benzyl,
    11. substituted benzyl wherein each substituent is loweralkyl of C₁–C₄, loweralkoxy of C₁–C₄, halo, nitro, trifluoromethyl, or cyano, there being from 1 to 5, both inclusive, substituents when each substituent is loweralkyl, loweralkoxy, or halo, and there being not more than 2 substituents when one substituent is nitro, trifluoromethyl, or cyano,
    12. decahydronaphthyl, or
    13. norbornyl; or
  b. when R⁰ and R¹ are taken together, they jointly constitute, with the nitrogen atom to which they are attached, a heterocyclic radical which is:
    1. piperidino,
    2. hexahydroazepino,
    3. octahydroazocino, or
    4. piperidino substituted by from 1 to 3 C₁–C₄, both inclusive, loweralkyl substituents, the total number of carbon atoms in all substituents being not in excess of 6.

2. The composition of claim 1 wherein the active agent is 4-(isopropylamino)-5,7-dinitro-2-trifluoromethylbenzimidazole.

3. The composition of claim 1 wherein the active agent is 4-(neopentylamino)-5,7-dinitro-2-trifluoromethylbenzimidazole.

4. The composition of claim 1 wherein the active agent is 4-(tert-butylamino)-5,7-dinitro-2-trifluoromethylbenzimidazole.

5. The composition of claim 1 wherein the active agent is 4-(1-ethyl-1-methyl-n-propylamino)-5,7-dinitro-2-trifluoromethylbenzimidazole.

6. The composition of claim 1 wherein the active agent is 4-(1,1,3,3-tetramethylbutylamino)-5,7-dinitro-2-trifluoromethylbenzimidazole.

7. The composition of claim 1 wherein the active agent is 4-(diisopropylamino)-5,7-dinitro-2-trifluoromethylbenzimidazole.

8. The composition of claim 1 wherein the active agent is 4-(1,2,2-trimethyl-n-propylamino)-5,7-dinitro-2-trifluoromethylbenzimidazole.

9. The composition of claim 1 wherein the active agent is 4-(tert-pentylamino)-5,7-dinitro-2-trifluoromethylbenzimidazole.

10. An insecticidal and arachnicidal composition which comprises an inert, finely divided solid and an insecticidally or anachnicidally-effective amount of a compound of the formula

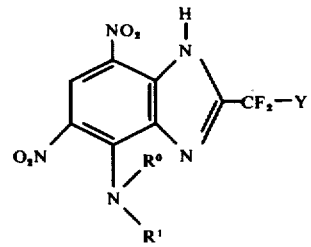

wherein Y represents
  a. hydrogen,
  b. chlorine,
  c. fluorine,
  d. trifluoromethyl, or
  e. pentafluoroethyl;
wherein
  a. when each of R⁰ and R¹ is taken separately, each independently represents, subject to the limitation that at least one of R⁰ and R¹ contains more than 1 carbon atom and that R⁰ and R¹ together contain less than 14 carbon atoms:

1. hydrogen,
2. alkyl,
3. alkenyl containing more than 2 carbon atoms,
4. alkynyl containing more than 2 carbon atoms,
5. (fluoroalkyl)methyl wherein alkyl is $C_1$–$C_7$, both inclusive, and bears at least one fluorine atom,
6. cycloalkyl of $C_3$–$C_8$, both inclusive,
7. cycloalkylloweralkyl, wherein cycloalkyl is from $C_3$–$C_8$, both inclusive, and loweralkyl is from $C_1$–$C_4$, both inclusive,
8. loweralkylcycloalkyl, wherein cycloalkyl and loweralkyl are as defined in the preceding candidate moiety,
9. adamantyl,
10. benzyl,
11. substituted benzyl wherein each substituent is loweralkyl of $C_1$–$C_4$, loweralkoxy of $C_1$–$C_4$, halo, nitro, trifluoromethyl, or cyano, there being from 1 to 5, both inclusive, substituents when each substituent is loweralkyl, loweralkoxy, or halo, and there being not more than 2 substituents when one substituent is nitro, trifluoromethyl, or cyano,
12. decahydronaphthyl,
13. norbornyl; or b. when R⁰ and R¹ are taken together, they jointly constitute, with the nitrogen atom to which they are attached, a heterocyclic radical which is:

1. piperidino,
2. hexahydroazepino,
3. octahydroazocino, or
4. piperidino substituted by from 1 to 3 $C_1$–$C_4$, both inclusive, loweralkyl substituents, the total number of carbon atoms in all substituents being not in excess of 6.

11. A method of controlling insects and arachnids which comprises contacting an insect or arachnid with an insecticidally or arachnicidally-effective amount of a compound of the formula

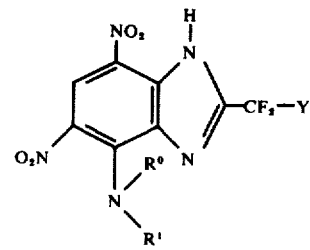

wherein Y represents
a. hydrogen,
b. chlorine,
c. fluorine,
d. trifluoromethyl, or
e. pentafluoroethyl;
wherein
a. when each of R⁰ and R¹ is taken separately, each independently represents, subject to the limitation that at least one of R⁰ and R¹ contains more than 1 carbon atom and that R⁰ and R¹ together contain less than 14 carbon atoms:
1. hydrogen,
2. alkyl,
3. alkenyl containing more than 2 carbon atoms,
4. alkynyl containing more than 2 carbon atoms,
5. (fluoroalkyl)methyl wherein alkyl is $C_1$–$C_7$, both inclusive, and bears at least one fluorine atom,
6. cycloalkyl of $C_3$–$C_8$, both inclusive,
7. cycloalkylloweralkyl, wherein cycloalkyl is from $C_3$–$C_8$, both inclusive, and loweralkyl is from $C_1$–$C_4$, both inclusive,
8. loweralkylcycloalkyl, wherein cycloalkyl and loweralkyl are as defined in the preceding candidate moiety,
9. adamantyl,
10. benzyl,
11. substituted benzyl wherein each substituent is loweralkyl of $C_1$–$C_4$, loweralkoxy of $C_1$–$C_4$, halo, nitro, trifluoromethyl, or cyano, there being from 1 to 5, both inclusive, substituents when each substituent is loweralkyl, loweralkoxy, or halo, and there being not more than 2 substituents when one substituent is nitro, trifluoromethyl, or cyano,
12. decahydronaphthyl, or
13. norbornyl; or
b. when R⁰ and R¹ are taken together, they jointly constitute, with the nitrogen atom to which they are attached, a heterocyclic radical which is:
1. piperidino,
2. hexahydroazepino,
3. octahydroazocino, or
4. piperidino substituted by from 1 to 3 $C_1$–$C_4$, both inclusive, loweralkyl substituents, the total number of carbon atoms in all substituents being not in excess of 6.

* * * * *

UNITED STATES PATENT AND TRADEMARK OFFICE
CERTIFICATE OF CORRECTION

PATENT NO. : 4,000,295
DATED : December 28, 1976
INVENTOR(S) : John L. Miesel

It is certified that error appears in the above-identified patent and that said Letters Patent are hereby corrected as shown below:

Column 1, line 44, "alkenyl" should read -- alkynyl --.

Column 18, line 22, number 100 should be under the Rate column and the number 9.0 should be under the Toxicity column.

Column 19, line 9, number 25 should be under the Rate column and the number 9.0 should be under the Toxicity column.

Column 19, line 39, number 100 should be under the Rate column and the number 8.5 should be under the Toxicity column.

Column 29, line 23, number 500 should be under the Rate column and the number 9.0 should be under the Toxicity column.

Column 31, line 11, number 250 should be under the Rate column and the number 8.5 should be under the Toxicity column.

Column 31, line 17, number 500 should be under the Rate column and the number 9.0 should be under the Toxicity column.

Column 36, line 14, number 100 should be under the Rate column and the number 8.0 should be under the Toxicity column.

Column 36, line 32, number 100 should be under the Rate column and the number 8.5 should be under the Toxicity column.

Signed and Sealed this

Nineteenth Day of April 1977

[SEAL]

Attest:

RUTH C. MASON
Attesting Officer

C. MARSHALL DANN
Commissioner of Patents and Trademarks